March 18, 1975 B. J. MACHIN Plant Pat. 3,691
CHRYSANTHEMUM PLANT
Filed July 23, 1973
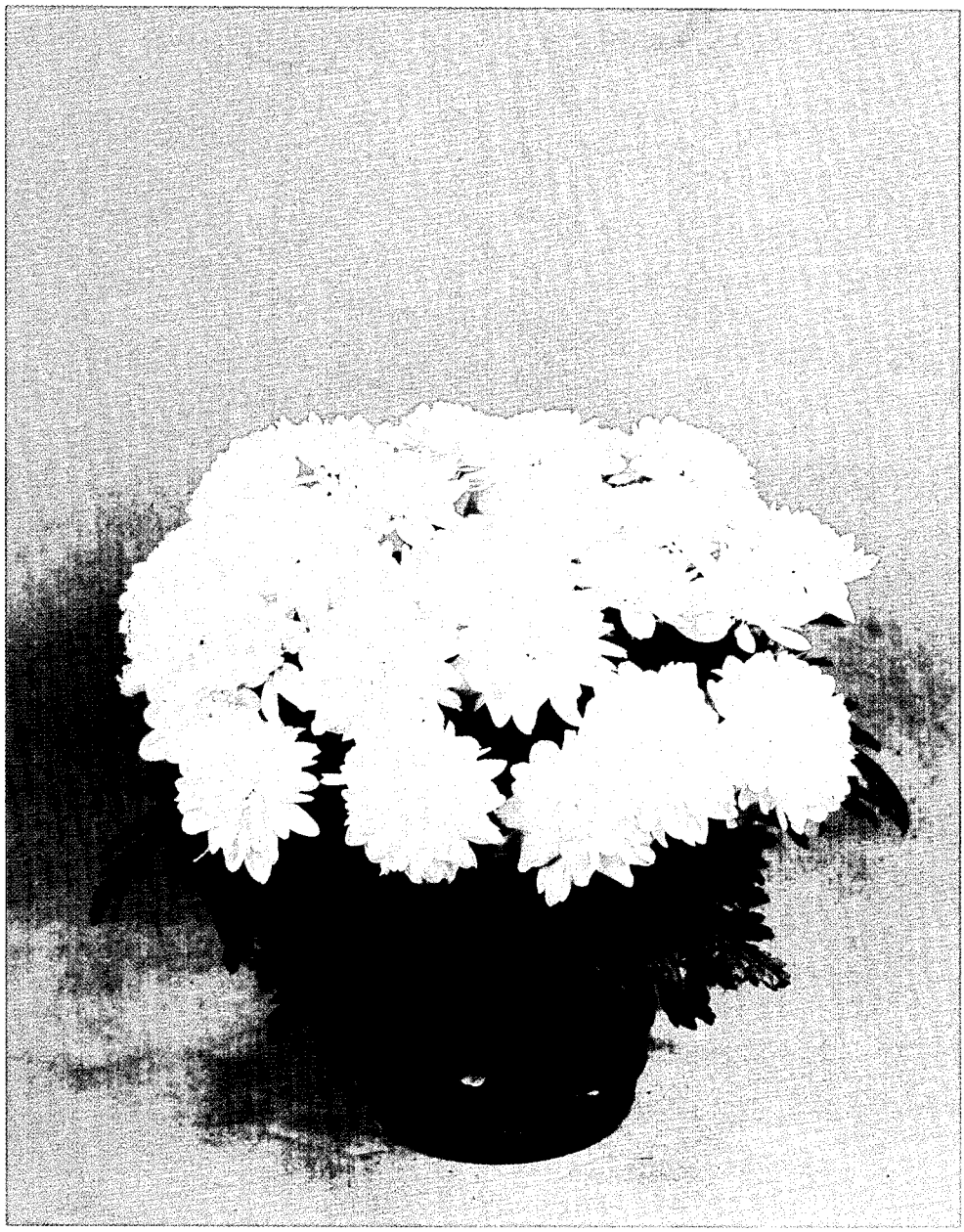

United States Patent

Plant Pat. 3,691
Patented Mar. 18, 1975

3,691
CHRYSANTHEMUM PLANT

Barrie John Machin, East Broyle Estate, Chichester, England, assignor to Framptons Nurseries Limited, Worthing, England

Filed July 23, 1973, Ser. No. 381,665
Int. Cl. A01h *5/00*
U.S. Cl. Plt.—78 1 Claim

ABSTRACT OF THE DISCLOSURE

This invention relates to a new and distinctive variety of *Chrysanthemum morifolium* Bailey (pot type) known as Yellow Popsie.

The new variety Yellow Popsie is a sport from a variety known as Popsie which was originated by me from a cross made in 1966 between the unpatented variety Bluebell and the unpatented variety Apricot Princess Anne, the former being the seed parent, and the latter being the pollen parent. The new variety Yellow Popsie was induced by irradiation from Popsie in July 1971.

The variety Popsie resulted from an extensive breeding program with the object of producing improved varieties for year round pot chrysanthemum production with particular emphasis on the need for improved varieties which can be used not only for the normal technique of production (4 or 5 cuttings in each pot), but also as single plant specimens in small pots. The variety Popsie has the following improved characteristics over the most similar existing varieties with which I am familiar:

1. It has an improved breaking action following a pinch so that a flowering shoot is produced from the majority of the leaf axils above the level of the compost.
2. It has good and uniform flowering whether or not the apical flower on each shoot is disbudded. This is not so with the large decorative varieties such as the Princess Anne family.
3. The lasting quality of the flowers is better than in varieties with longer, softer petals.
4. The small pompon-like flowers are hard and crisp and withstand adverse marketing conditions better than most existing varieties.

The habit of the plant is more ideal (i.e. stocky and well branched) for the production of small pots using single plants.

The variety Yellow Popsie is similar to the variety Popsie in the above characteristics and differs from it only in color of flower, which is yellow rather than purple.

The accompanying drawing shows a typical flower of my new variety depicted in color as nearly true as it is reasonably possible to make the same in a color illustration of this character.

Asexual reproduction of this new variety Yellow Popsie as performed in Sussex, England, by rooting vegetation shoots, shows that the above characteristics are fixed and come true to type through succeeding generations.

The following is a detailed description of the new variety Yellow Popsie with color terminology in accordance with the Royal Horticultural Society color chart, hereinafter referred to as RHS.

Genus: Chrysanthemum.
Species: *Morifolium* Bailey.
Type: Pot.
Class: Pompon (or small incurving decorative).
Breeding: The original variety Popsie resulted from a cross between the variety BGA Bluebell and the variety Apricot Princess Anne, the former being the seed parent, the latter being the pollen parent. The cross was made in 1966 at Framptons Nurseries, Forbridge Nursery, Chichester, Sussex, England. The variety Yellow Popsie was induced by irradiation from the variety Popsie in July 1971, in Sussex, England.
Propagation: Holds its distinguishing characteristics through succeeding generations by rooting vegetative shoots.
Flower: When grown and observed in Sussex, England, and produced as single plants in 3½ in. pots, pinching induces the formation of up to 10 flowering shoots. When produced as a 5½ in. pot plant using 5 cuttings per pot each plant produces 3 to 6 flowering shoots following a pinch.
Size: Average diameter is 7 cms. when fully open.
Petallage: Approximately 350 ray petals and 10 disc petals.
Form: A small incurving decorative or pompon.
Petals: Short, broad, boat shaped, thick, and of very firm texture.
Color of open bloom:
*Inner face of fully expanded petal.*—RHS 5B.
*Outer face of fully expanded petal.*—RHS 5C.
*Inner face of young petal.*—RHS 5A.
*Outer face of young petal.*—RHS 5B.
Response group: 10 weeks.
Temperature tolerance: 57 to 60 F. at night.
Plant: Short, stocky and free branching, very suitable for single plant types.
Foliage: Medium size and light green. Color RHS 138A.
Stem: Thick and strong. Color RHS 139D at flowering.

I claim:

1. A new and distinct variety of *Chrysanthemum morifolium* Bailey, substantially as shown and described, characterized particularly as to novelty by the unique combination of a yellow color; small, hard and crisp pompon-like flowers, the production of a flowering shoot from a majority of the leaf axils above the compost level following a pinch; and good, uniform flowering regardless of whether the apical flower on each shoot is disbudded.

No references cited.

ROBERT E. BAGWILL, Primary Examiner